(12) United States Patent
Lei (10) Patent No.: US 10,695,517 B2
(45) Date of Patent: Jun. 30, 2020

(54) NASAL BREATHING APPARATUS AND METHOD WITH MULTIFUNCTION

(71) Applicant: Baiping Lei, Staten Island, NY (US)

(72) Inventor: Baiping Lei, Staten Island, NY (US)

( * ) Notice: Subject to any disclaimer, the term of this patent is extended or adjusted under 35 U.S.C. 154(b) by 453 days.

(21) Appl. No.: 15/789,966

(22) Filed: Oct. 21, 2017

(65) Prior Publication Data
US 2018/0043123 A1 Feb. 15, 2018

Related U.S. Application Data

(62) Division of application No. 14/997,631, filed on Jan. 18, 2016, now Pat. No. 9,827,392.

(51) Int. Cl.
| | |
|---|---|
| *A61M 16/06* | (2006.01) |
| *A61M 16/08* | (2006.01) |
| *A61M 16/00* | (2006.01) |
| *A61M 16/01* | (2006.01) |

(52) U.S. Cl.
CPC .... *A61M 16/0666* (2013.01); *A61M 16/0057* (2013.01); *A61M 16/01* (2013.01); *A61M 16/0616* (2014.02); *A61M 16/0683* (2013.01); *A61M 16/085* (2014.02); *A61M 16/0875* (2013.01); *A61M 2202/0208* (2013.01); *A61M 2230/432* (2013.01)

(58) Field of Classification Search
CPC .......... A61M 16/0666; A61M 16/0616; A61M 16/085; A61M 16/0057; A61M 16/01; A61M 16/0683; A61M 16/0875; A61M 2202/0208; A61M 2230/432
See application file for complete search history.

(56) References Cited

U.S. PATENT DOCUMENTS

| | | | |
|---|---|---|---|
| 4,054,133 A | * | 10/1977 | Myers ................... A61M 16/20 128/204.26 |
| 4,265,239 A | | 5/1981 | Fischer, Jr. |
| 4,367,735 A | | 1/1983 | Dali |
| 4,535,767 A | | 8/1985 | Tiep et al. |
| 5,280,780 A | | 1/1994 | Abel |
| 5,335,656 A | | 8/1994 | Bowe |
| 5,533,506 A | | 7/1996 | Wood |
| 6,431,172 B1 | * | 8/2002 | Bordewick ....... A61M 16/0666 128/206.11 |
| 6,848,446 B2 | | 2/2005 | Noble |

(Continued)

*Primary Examiner* — Timothy A Stanis
*Assistant Examiner* — Jonathan S Paciorek
(74) *Attorney, Agent, or Firm* — Walter J. Tencza, Jr.

(57) ABSTRACT

A nasal breathing apparatus with multifunction has two nasal inserts and one tubular chamber. In one embodiment, the first nasal insert forms an airtight barrier inside one nostril for delivering gases. The second nasal insert does not block the other nostril and is for sampling gases. The tubular chamber is in fluid communication with the first nasal insert but not the second nasal insert and has an outlet for discharging and delivering gases and for providing continuous positive airway pressure and ventilation. In another embodiment, both nasal inserts form an airtight barrier in the corresponding nostrils. The first nasal insert is dedicated for delivering gases and the second nasal insert for sampling gases. The tubular chamber is in fluid communication with both nasal inserts and has an outlet for discharging and delivering gases and for providing continuous positive airway pressure and ventilation.

16 Claims, 4 Drawing Sheets

(56) References Cited

U.S. PATENT DOCUMENTS

| | | |
|---|---|---|
| 7,195,018 B1 | 3/2007 | Goldstein |
| 7,353,826 B2 | 4/2008 | Sleeper et al. |
| 8,161,971 B2 | 4/2012 | Jaffe |
| 8,631,799 B2 | 1/2014 | Davenport et al. |
| 8,707,950 B1 | 4/2014 | Rubin |
| 2002/0112730 A1* | 8/2002 | Dutkiewicz ......... A61M 16/085 128/207.18 |
| 2004/0015092 A1 | 1/2004 | Pettersson |
| 2004/0103899 A1* | 6/2004 | Noble .................. A61M 16/01 128/207.18 |
| 2005/0028822 A1* | 2/2005 | Sleeper ................ A61M 16/06 128/207.18 |
| 2006/0107958 A1* | 5/2006 | Sleeper ............. A61M 16/0666 128/206.11 |
| 2008/0223375 A1 | 9/2008 | Cortez et al. |
| 2010/0252037 A1* | 10/2010 | Wondka ............ A61M 16/0003 128/203.12 |
| 2011/0009763 A1 | 1/2011 | Levitsky |
| 2011/0094518 A1* | 4/2011 | Cipollone ......... A61M 16/0666 128/207.18 |
| 2011/0214676 A1 | 9/2011 | Allum |
| 2012/0204870 A1 | 8/2012 | McAuley |
| 2012/0255553 A1 | 10/2012 | Wood |
| 2013/0160772 A1 | 6/2013 | Tabrizchi |
| 2014/0018691 A1 | 1/2014 | McNeil |
| 2014/0066801 A1 | 3/2014 | Tero |
| 2014/0276169 A1 | 9/2014 | Chua |
| 2014/0366880 A1 | 12/2014 | Metz |
| 2015/0013678 A1* | 1/2015 | McAuley ......... A61M 16/0666 128/203.22 |
| 2015/0230731 A1 | 8/2015 | Levitsky et al. |
| 2016/0158476 A1 | 6/2016 | Tatkov |

\* cited by examiner

NASAL BREATHING APPARATUS AND METHOD WITH MULTIFUNCTION

CROSS REFERENCE TO RELATED APPLICATION(S)

The present application is a divisional of and claims the priority of U.S. patent application Ser. No. 14/997,631 titled "NASAL BREATHING APPARATUS AND METHOD WITH MULTIFUNCTION", filed on Jan. 18, 2016.

FIELD OF THE INVENTION

The present invention relates generally to the field of respiratory therapy and anesthesia. More particularly, the present invention relates to apparatus and methods for delivering gases and providing continuous positive airway pressure (CPAP) and ventilation to a patient through the nose.

BACKGROUND OF THE INVENTION

Hypoxemia is a life threatening event that frequently occurs in all patient care areas, especially in operating room (OR), procedural room outside the OR, post anesthesia care unit (PACU), emergency room (ER), and intensive care unit (ICU) settings. Patients in these settings either receive medications (such as anesthetics, analgesics, and sedatives) that can cause apnea and respiratory depression or have acute or chronic diseases that can cause hypoxemia. Supplementing oxygen or providing assisted ventilation is an essential approach to avoiding hypoxemia and maintaining adequate oxygenation.

A wide variety of devices, such as nasal cannula, face mask, and nasal mask, are available to deliver oxygen therapy for non-intubated patients. Face masks and nasal masks are commonly used to deliver high flow of oxygen but are not well tolerated by patients (especially those patients with claustrophobia). To deliver high concentrations of oxygen, a good mask-to-face/nose seal has to be attained and the pressure on the nose and face causes considerable discomfort for a patient. A nasal cannula is a simple, benign, and inexpensive device. It is widely used and well tolerated by the majority of patients and valuable for patients who do not require a high Fraction of Inspired Oxygen ($FiO_2$) and who are unable to tolerate face or nasal masks. However, existing nasal cannulas allow neither administering high flow of oxygen, since they can only provide a flow rate of oxygen up to six liters per minute (lpm), nor do they provide assisted ventilation. Existing nasal cannulas are inefficient for delivering gases because most of the delivered gases are wasted and only a small percentage of the delivered gases actually reach the nasal airway of a patient. Additionally, the suction force generated by a gas analyzer draws the mucosal tissues onto the tip of nasal prong, and causes frequent occlusion, itching and discomfort. They are also easily dislodged and moved away from the nostrils of a patient.

To overcome some drawbacks of a conventional nasal cannula, several modified nasal cannula systems have been proposed to improve the efficiency of oxygen delivery or to deliver high flow of oxygen. The reservoir nasal cannula by Tiep et al., disclosed in U.S. Pat. No. 4,535,767, and marketed by Chad Therapeutic, Inc, known as the Oxymizer (trademarked), mustache style and pendant style, has a small reservoir (about twenty milliliters volume) to store oxygen during exhalation and save oxygen. The ability to conserve oxygen is limited due to the limited volume of the reservoir and the air dilution during the inhalation.

Another oxygen delivering and conserving device, proposed by Abel in U.S. Pat. No. 5,280,780, has a larger oxygen storage chamber and does not allow exhaled gases to mix with delivered oxygen. Abel's device may save more oxygen during exhalation and allow delivering higher concentration of oxygen. However, the nasal prongs of the devices of both Abel and Tiep et al. are open to the air and cannot avoid the dilution of oxygen from the air entrain during inhalation. Thus, they do not allow administering high flow of oxygen to meet a patient's need.

Another nasal cannula, disclosed by James Chua in US published patent application 2014/0276169 A1, has divided flow paths allowing insufflating oxygen through one of the nostrils and collecting the exhaled gases from the other nostril. The nostril that is used for insufflating gases is blocked by an insufflating nare with a one-way valve, which allows supplying oxygen from the insufflating nare during inhalation only but not during exhalation. The other nostril is dedicated for sampling the exhaled gases via a sampling nare that does not block the nostril. This device allows delivering low flow of oxygen and conserving oxygen while allowing sampling an undiluted sample of end tidal carbon dioxide ($ETCO_2$) contained within the exhaled gases from the patient. However, it does not provide other desired functions, such as delivering high flow of gases, attaining CPAP and providing positive pressure ventilation.

The Optiflow (trademarked) nasal cannula interface, manufactured by Fisher & Paykel Healthcare Inc., is for delivering high flow of air/oxygen to a patient's nose. This delivery system can deliver heated and humidified air/oxygen by a device called the "AIRVO 2" (trademarked) at a rate of two to sixty liters per minute (lpm) and provide nasal insufflation. Nasal insufflation with high flow of air/oxygen has shown several beneficial effects, such as decreasing work of breathing, improving ventilation efficiency, reducing the need for intubation in patients with respiratory insufficiency, and preventing post-extubation failure. The exact mechanisms are unclear but it builds up CPAP and can treat mild and moderate sleep apnea. The "AIRVO 2" (trademarked) has been used for pre-oxygenation and apneic oxygenation during routine anesthesia induction or emergency intubation and significantly decreases the incident of hypoxemia during efforts securing an endotracheal tube. It has also been shown that initiation of nasal insufflation with high flow of air/oxygen immediately following extubation reduces the risk of reintubation. Although post-extubation non-invasive ventilation (NIV) remains the first-line approach when indicated, nasal insufflation may be an attractive alternative to NIV for patients who aren't candidates for post-extubation NIV or who are unable to tolerate NIV. Unlike NIV, nasal insufflation allows patients to talk and expectorate secretions. However, the Optiflow (trademarked) nasal cannula is open to air (occludes no more than 50% of a nostril) and high flow rates of oxygen are required to prevent air entrain during inhalation. A special device that can heat and humidify the air/oxygen is required and not readily available in all of the patient care areas.

Obstructive sleep apnea (OSA) is a common sleep disorder that occurs when a person's breathing is interrupted during sleep. The patients with OSA have a significantly increased risk of respiratory complications perioperatively. Continuous positive airway pressure (CPAP) and other non-invasive positive pressure ventilation (NIPPV) techniques have demonstrated clinical benefits in patients with OSA and have become the standard of care in the hospital environment. A CPAP system typically consists of a CPAP machine (a gases supply), a conduit tube, and a nasal or face mask. The nasal or face masks are uncomfortable to wear because of the pressures applied on the face and the nose. Several nasal interfaces have been proposed to replace nasal or face masks for attaining CPAP. They are more comfortable to wear and have increased patient comfort and compliance. These nasal interfaces include Nasal Aire II (trademarked) (invented by Thomas J. Wood and manufactured by InnoMed Technologies, Inc), Bravo (trademarked) nasal pillow CPAP mask (invented by and manufactured by InnoMed Technologies, Inc), Swift TM FX (trademarked) nasal pillow (manufactured by ResMed) and AirFit P10 (trademarked) nasal pillow (ResMed). They completely seal the nostrils and prevent air leakage during inhalation and exhalation. They can attain CPAP and provide positive pressure ventilation if needed. However, they are designed for delivering CPAP and treating OSA. A CPAP machine is needed. It is also difficult to deliver high flow of oxygen via these nasal pillows without significant modifications. Most of conscious patients may be not comfortable with both nostrils being blocked. Another nasal interface (NVA SNOR-TAL R (trademarked) options, by Noble Anesthesia-Air Inc.) is designed for delivering positive airway pressure from an anesthesia circuit. It is self-sizing, self-retaining and self-sealing within the nasal vestibule (from the company's website). It also gives the anesthesia practitioner unencumbered access to the mouth. One of the major disadvantages is that it has to be used with an anesthesia circuit and cannot be used in the settings without an anesthesia machine.

In summary, existing nasal breathing devices can only provide one or two desired functions and do not have multifunction to meet the requirements of patients and clinicians. Thus, there is a need for a single nasal breathing device that can have multifunction to meet the patient's needs.

SUMMARY OF THE INVENTION

One or more embodiments of the present invention provide one or more devices and methods for delivering low flow or high flow of gases, monitoring end tidal carbon dioxide ($ETCO_2$), delivering aerosol medications, and providing continuous positive airway pressure (CPAP) and positive pressure ventilation.

It is an object of one or more embodiments of the present invention to provide a simple, disposable, and inexpensive multifunctional nasal breathing apparatus and method that can be used in the majority of awake inpatients or ambulatory patients for delivery of gases, spontaneous respiration monitoring, aerosol medication delivery, CPAP, and assisted positive pressure ventilation.

It is an object of one or more embodiments of the present invention to provide a nasal breathing apparatus and method that can conserve oxygen and allow accurate monitoring of $ETCO_2$ when low flow or high flow of oxygen are delivered. In at least one embodiment, a device is provided comprising a main piece of apparatus having two nasal inserts and one tubular chamber. One nasal insert or both nasal inserts are constructed in a way that can fit snugly inside the nostrils of a patient and form an airtight barrier. The tubular chamber is in fluid communication with one or both nasal inserts and has a built-in tubing or channel for delivering gases and an outlet for discharging exhaled gases. The delivered gases are directed to the patient's the nasal airway through one nostril and the exhaled gases are discharged through both nostrils. There is no gas leak from the nostril. The tubular chamber also can serve as an oxygen reservoir during exhalation. Thus, the delivered gases are less likely to be wasted and a much lower flow rate of oxygen is needed to achieve adequate oxygen supply. Since, in at least one embodiment, the second nasal insert is solely for sampling the exhaled gases, the exhaled gases are less likely diluted from the delivered gases. This will allow more accurate monitoring of $ETCO_2$. Furthermore, in at least one embodiment, the second nasal insert is a flexible corrugated tube that can be flexed or bent in any part and maintained at an optimal position. The tip of the second nasal insert does not have to directly contact the inner wall of the nostril. It will reduce the likelihood of occlusion and discomfort.

It is another object of one or more embodiments of the present invention to provide a device, apparatus and/or method that can prevent the leakage of oxygen from the nose and decrease the risk of combustion in the surgical field near the face when using electrical cautery or laser devices while supplemental oxygen is deemed necessary. The nasal insert that is dedicated for oxygen delivery forms an airtight barrier inside one of the nostrils of a patient or person and prevents the escape of oxygen from that particular nostril. By attaching a flexible extendable tube adapter to an outlet of a tubular chamber, the excessive delivered oxygen can be scavenged from the device and less likely accumulates around the face. Although monitoring the exhaled oxygen concentration is still needed, this will decrease the risk of fire in the surgical field. It will also decrease the frequent need for correcting hypoxemia during the procedure and will have less interruptions with the surgical procedure.

It is another object of one or more embodiments of the present invention to provide a device, apparatus, and/or method that can achieve nasal insufflation with high flow of oxygen when high concentration of oxygen is needed. At least one embodiment of the present invention provides a device with a large bore (In an adult, the inner diameter may be up to about six to eight millimeters (mm)) oxygen supplying tubing or channel within the tubular chamber and the nasal insert which is dedicated for delivering gases. The oxygen flow rate can reach fifteen to twenty liters per minute (lpm) with a single oxygen supplying source such as a conventional wall oxygen flow meter, an oxygen tank, or an anesthesia machine. An outlet of a tubular chamber also can be connected to another oxygen source and the total flow rate can reach forty to fifty liters per minute (lpm). A device in accordance with at least one embodiment, can be used in patients who undergo general anesthesia or who need endotracheal intubation when hypoxemia is the main concern. The patients can comfortably wear at least one embodiment of a device of the present invention for preoxygenation prior to intubation. This allows continuously supplying of oxygen during airway management. This will significantly reduce the incidents of hypoxemia. Unlike a face mask, one or more embodiments of the present invention allow a patient to talk during preoxygenation and thus are more likely to be accepted by the patient. It is safe to use high flow of oxygen without humidification for a short period of time. Since there is no leakage of oxygen from the nose, in one or more embodiments, a much lower flow rate of oxygen is needed for achieving nasal insufflation. Thus, nasal insufflation can be achieved without a special machine or device.

It is another object of one or more embodiments of the present invention to provide a device that can deliver aerosol medications to a patient's respiratory tract. In the PACU or other hospital settings, some patients may need to receive aerosol medications via a nebulizer for treating airway edema, asthmatic attacks, or heart failure. The conventional methods use either a face mask or a mouthpiece. With a device in accordance with one or more embodiments of the present invention, a nebulizer can be attached to the gas supplying tubing or the outlet of the tubular chamber via a flexible extendable tube adapter. Additional face mask or mouthpiece is not needed. The patient can talk and expectorate secretions while receiving the therapy. It is more easily applied and more likely accepted by the patients, especially children. The disclosed device does not require the patient to breathe through the mouth while receiving the treatments. The aerosol medications are passively delivered through the nasal airway and inhaled by the patient. Also less medication will be wasted. This will greatly increase treatment compliance and efficiency.

It is another object of one or more embodiments of the present invention to provide a device that can be used for airway preparation for awake fiberoptic intubation. Adequate airway anesthesia is a prerequisite for successful awake fiberoptic intubation. The anesthesiologists usually attach a nebulizer to a face mask or a mouthpiece to deliver nebulized topic anesthetics (such as lidocaine) to a patient's airway. The use of a mouthpiece requires a patient's cooperation and the face mask causes discomfort. A device in accordance with one or more embodiments of the present invention can deliver nebulized topical anesthetics to a patient's airway during inhalation and exhalation and allow communicating with the patient during the preparation. This will significantly decrease the patient discomfort and anxiety while achieving a good airway anesthesia.

It is another object of one or more embodiments of the present invention to provide a device that can be used for anesthesia induction and/or maintenance by delivering anesthetic gases (such as nitrous oxide and sevoflurane) via the nose. Although intravenous anesthesia induction is the first choice for most of the adult patients and older children, inhalational induction with a face mask is a frequently used induction technique for younger children or uncooperative patients without an intravenous access. The use of a face mask requires a tight mask-to-face seal and causes a significant discomfort to the patient and anesthetic air pollution. Most of the patients have been fighting before loss of consciousness, which makes inhalational induction process very stressful and dangerous. With a device in accordance with one or more embodiments of the present invention, an anesthesia circuit can be attached to the gas supplying tubing or the outlet of the tubular chamber via a flexible extendable tube adapter. Inhalational agents can be delivered into the airway via the nose without using a face mask. The patient can talk and communicate with physicians during induction. It may be more easily applied and more likely accepted by patients, especially children. A device in accordance with one or more embodiments of the present invention can also be used for anesthesia induction and/or maintenance for short surgical procedures or office-based anesthesia such as in a dental office. Since there is no leakage of gases from the nose and the excessive delivered gases can be easily scavenged, in one or more embodiments, it will reduce anesthetic air pollution.

It is another object of one or more embodiments of the present invention to provide a device that can attain CPAP by attaching a CPAP valve or positive end-expiratory pressure (PEEP) valve to the outlet of the tubular chamber via a flexible extendable tube adapter and connecting a gas supplying conduit to the gas supplying tubing of the device. In one of the embodiments of the present invention in which the other nostril is not blocked by a second nasal insert, the nostril can be blocked by a nasal plug. A device in accordance with one or more embodiments of the present invention can be connected to an anesthesia machine and critical care circuits or a standard CPAP machine. A moderate level of CPAP (eight to ten centimeters (cm) $H_2O$) can be obtained with a gas flow rate of twenty to thirty liters per minute (lpm) even without a CPAP machine. This one-sided nasal CPAP allows the patient to place the nasal insert inside the nostril he or she wants and to switch nostrils at any given time intervals. One nostril is sufficient to provide all of the air required by the patient and to allow discharging the exhaled gases. In fact, most of humans only breathe out of one nostril at a time. Unlike other CPAP delivery systems that require the patient to wear a support device and are uncomfortable to wear, the disclosed device has more flexibility and is more comfortable for the patients. The common side effects of nasal CPAP such as dryness of nose and nasal congestion can be reduced by switching the nostrils periodically. It will enhance patient comfort, flexibility and compliance. It can be used in the hospital settings or in a home environment.

It is yet another object of one or more embodiments of the present invention to provide a device that can achieve nasal positive pressure ventilation with readily available devices such as an anesthesia machine or a resuscitator bag (Ambu (trademarked) bag or generically a manual resuscitator or self-inflating bag) in patients with weak or ineffective spontaneous breathing. During monitored anesthesia care, patients frequently become apneic or breathe ineffectively because of oversedation. Most of the time only a short period of assisted positive pressure ventilation is needed to correct hypoxemia. The disclosed device can be used to provide positive pressure ventilation and relieve mild/moderate airway obstruction. Additional face mask or nasal mask is not needed. This will greatly decrease the need for invasive airway management and increase patient safety.

DETAILED DESCRIPTION OF THE DRAWINGS

In order to assist in the understanding of the features and advantages of embodiments of the present invention, the following detailed description of the exemplary embodiments should be considered in conjunction with the accompanying drawings. One or more embodiments of the present invention provide a novel nasal breathing device with multifunction. The preferred embodiments of the present invention will now be described with references to the drawings. The drawings are not necessarily to scale and mainly used to illustrate principles of the present invention.

Figure 1:
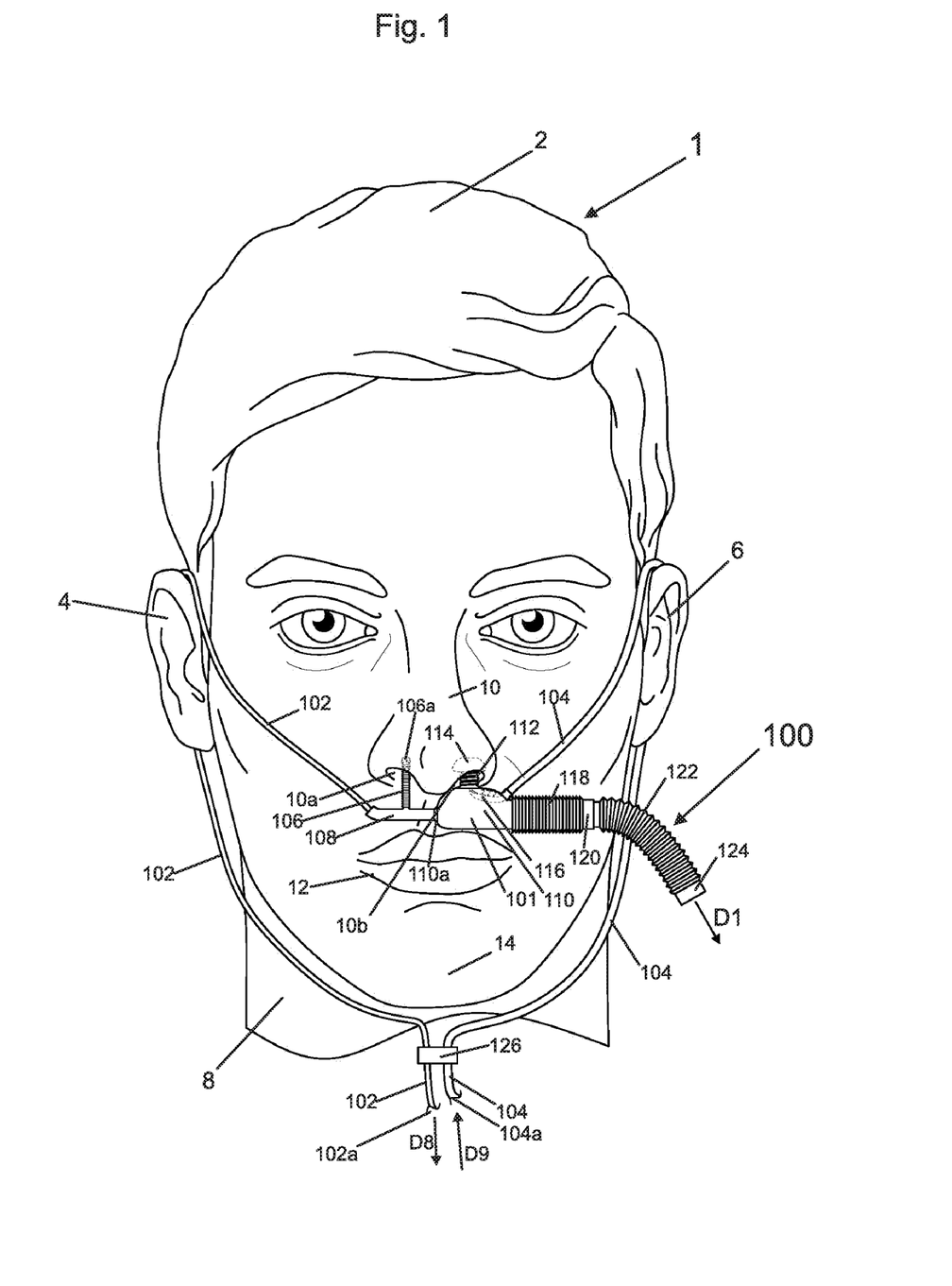
FIG. 1 shows a simplified diagram of a front view of a nasal breathing apparatus in accordance with an embodiment of the present invention being worn by a patient.

With reference to FIG. 1, an apparatus 100 of a first embodiment of the present invention is shown in which a patient 1 having a head 2 is wearing the apparatus 100. The patient or person 1 may have a head 2, ears 4 and 6, neck 8, nose 10, a mouth 12, and a chin 14. The nose 10 of the patient or person 1 may include nostrils 10a and 10b.

The apparatus 100 includes a main portion 101, gas supply tubing 104, and gas sampling tubing 102.

The main portion 101 is placed on the face of the patient or person 1 beneath the nose 10 and above the upper lip of the mouth 12 and is secured on the face of the person 1 with a loop formed by the gas supplying tubing 104 and the gas sampling tubing 102 hung on the back of the ears 6 and 4, respectively. The loop is tightened to the patient's head 2 by sliding a bolo type tie 126 or the like towards the patient's chin 14. The first nasal insert 114 is at least partially inserted into the left nostril 10b and forms an airtight barrier. The second nasal insert 106 is placed into the right nostril 10a and does not block the nostril 10a. Oxygen or gases are delivered to the nasal airway via the first nasal insert 114. Exhaled gases are discharged from the first nasal insert 114 and the right nostril 10a and sampled via the second nasal insert 106. An outlet 120 of the tubular chamber 110 is attached to a flexible extendable tube adapter 122 for discharging exhaled gases from the first nasal insert 114 or attaining CPAP/positive pressure ventilation.

Figure 2:
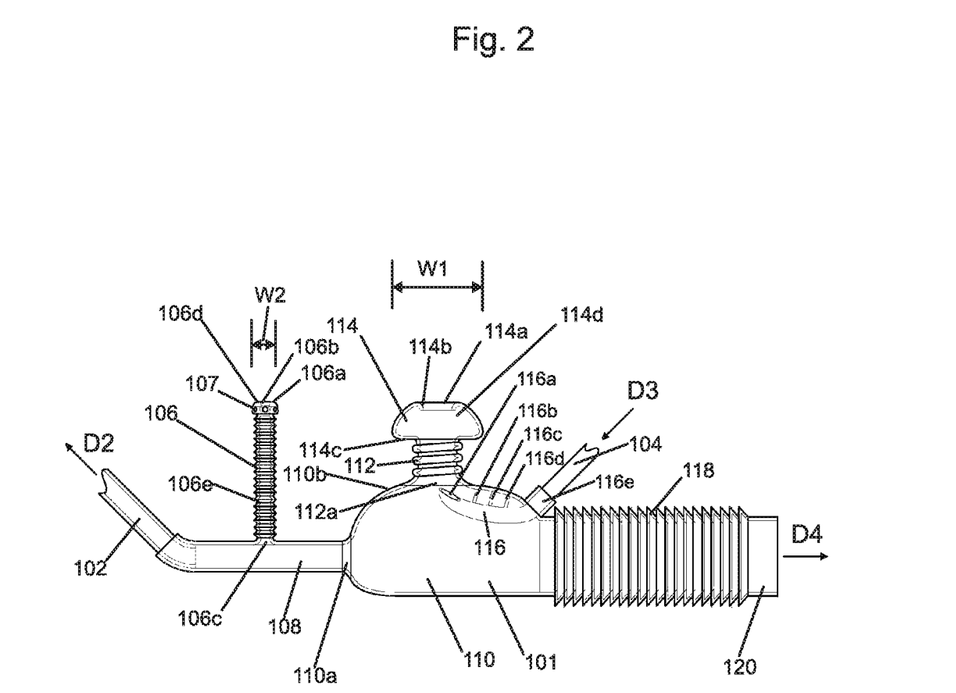
FIG. 2 shows a simplified diagram of a front view of part of the nasal breathing apparatus of FIG. 1.

Generally speaking, referring to FIG. 1, gases flow in the direction D9 into end 104a of tubing 104, through tubing 104, into chamber 110, and out component 114, into the nasal airway. In addition, excessive gases and/or exhaled gases flow out of the chamber 110 through components 118, 122 and 124 and out in the direction D1. In addition, gases flow from the nostril 10a into component 106, then into component 108, then into tubing 102, and out end 102a of the tubing 102 in the direction D8. Fluids or gasses do not pass between component 108 and 110, but rather are kept separate by stop, block, or solid component 110a. FIG. 2 shows a simplified diagram of a front view of part of the nasal breathing apparatus 100 of FIG. 1, which includes main portion 101. The main portion 101 of the apparatus 100 includes four main members: the first nasal insert 114, the second nasal insert 106, the tube 108, the tubular chamber 110. The tubular chamber 110 is in fluid communication with the first nasal insert 114 but not the second nasal insert 106.

Generally speaking, as shown in FIG. 2, gases flow in tubing 104 in the direction D3, flow in the tubing 102 in the direction D2, and flow out of component 120 in the direction D4.

The first nasal insert 114 and the second nasal insert 106 are formed integrally with the tubular chamber 110 and the tube 108 and manufactured from one or two non-irritating soft inert materials, such as silicone, or the like. Alternatively, they can be made separately and molded together. They should be soft, compliant, flexible, resilient, crush-resistant, and transparent or semi-transparent.

The first nasal insert 114 includes a top portion 114d, a tube 112 and a base 110b. The base 110b is also a part of the top wall of the tubular chamber 110. The top portion 114d of the first nasal insert 114 is formed in a mushroom shape with a large opening 114a at its first open end and fits into the user's nostril 10b as show in FIG. 1. The sizes of the top portion 114d may vary. For an adult, the bottom part 114c of the mushroom-shaped top portion 114d preferably has an outer diameter of about 10 to 16 mm and the opening 114a preferably has an outer diameter of about 50 to 70% of the width of the bottom part 114c. The length of the mushroom-shaped top portion 114d (the distance from the opening 114a to the bottom part 114c) preferably is equal to about 50 to 70% of the width of the bottom part 114c. When the top portion 114d is inserted into the nostril 10b, the bottom part 114c will be preferably inside the nostril 10b. The opening 114a of the top portion 114d has an inward rolled rim 114b shown in FIG. 2. The inward rolled rim 114b and the top portion 114d of the first nasal insert 114 are made from soft, flexible, resilient silicone, or the like and thin-walled. The inward rolled rim 114b, in at least one embodiment, should be very soft and contact the mucous membrane of the nasal cavity in the nostril 10b, which forms a first physical sealing interface between the surface of the inward rolled rim 114b and the mucous membrane. The inward rolled rim 114b configuration makes the first nasal insert 114 less stimulating and more comfortable. As an alternative, the opening 114a can have an outward rolled rim. The top portion or section 114d can comfortably fit into the user's nose 10 and forms a second physical sealing interface between the outer surface of the top portion or section 114d and the inner wall of the nostril 10b. It prevents the dislodgement of the top portion or section 114d of the first nasal insert 114 in general from the nostril 10b because the bottom 114c of the mushroom-shaped top portion 114d is larger (in diameter and/or width W1) than the opening of the user's nostril 10b. The top portion or section 114d is compressible and/or deformable allowing the bottom 114c fit into nostril 10b even though section 114d may be wider in width W1 than the width of the nostril 10b. The second open end 112a of the first nasal insert 114 is in fluid communication with the tubular chamber 110, which means that the delivered gases from the built-in tubing or channel 116 can enter the nasal airway via the first nasal insert 114 and the exhaled gases and excessive delivered gases from the nostril 10b can flow through the first nasal insert 114, into chamber 110.

It is appreciated that the top portion 114d of the first nasal insert 114 can be formed in any other shape as long as it seals the nostril 10b and does not cause significant discomfort. However, a mushroom shape with an inward rolled rim, such as 114b is preferred. The mushroom-shaped top portion 114d is gradually increased in diameter from its top at opening 114a (about six to ten millimeters in outer diameter) to its bottom 114c (about ten to sixteen millimeters in outer diameter). When the first nasal insert 114 is at least partially inserted into the nostril 10b, the inward rolled rim 114b may contact the inner wall of the nostril 10b first and forms a physical sealing interface. If the first nasal insert 114 is further pushed into the nostril 10b, it always can reach a position where the cross-section of any part of the top portion 114d of the first nasal insert 114 matches the cross-section of the nostril 10b and forms an airtight barrier.

The top portion 114d of the first nasal insert 114 may be constructed of any non-irritating and inert material apparent to those having skill in the relevant art(s) after reading the description herein. It is thin-walled, soft, compliant, resilient, compressible, deformable, and expandable. It can expand under the positive pressure of incoming gases. Thus, the top portion 114d of the first nasal insert 114 will fit and seal different anatomical sizes and shapes for nostril 10b for different persons. The unique configuration of the top portion 114d will provide a very comfortable fit in the nostril and create an airtight seal to prevent the leakage of gases.

The base 110b of the first nasal insert 114, in at least one embodiment, continues, and/or is integral with the top side of the tubular chamber 110 and is formed in a mushroom shape or in a dome shape. The height or depth of the mushroom-shaped or the dome-shaped base 110b preferably is equal to or slightly larger than the outer diameter of the built-in tubing or channel 116, so that most part of the built-in tubing or channel 116 is located inside the base 110b. The mushroom-shaped or the dome-shaped base 110b will expand under the positive pressure of incoming gases and seal the opening of the nostril 10b of the nose 10. The base 110b also creates an upward force against the nose 10 when the loop formed by the gas supplying tubing 104 and the gas sampling tubing 102 is hung on the back of the head 2 or the ears 6 and 4, respectively. This configuration will increase the size of the gas flow path inside the first nasal insert 114 which allows simultaneously accommodating a large bore gas supplying tubing or channel 116 shown in FIG. 2 and discharging the exhaled gases from the same nostril 10b via the first nasal insert 114. Generally, exhaled gases are discharged from the same nostril 10b via the first nasal insert 114 and the other nostril 10a. When the other nostril 10a is blocked, both inhaled and exhaled gases will be through one nostril 10b.

The nasal insert 114 includes a portion or tube 112 between the top portion 114d and the base 110b. The portion or tube 112 preferably has an inner diameter equal to the inner diameter of the opening 114a or ten to fifteen percent larger than the inner diameter of the opening 114a. So the incoming gas flow will produce a positive pressure inside the mushroom-shaped top portion 114d and help form an airtight barrier in the nostril 10b. The portion or tube 112, in at least one embodiment, is formed in a spirally corrugated shape. The spirally corrugated configuration will provide good flexibility and elasticity and allow adjusting the direction and position of the first nasal insert 114. The portion 112, in at least one embodiment, is flexible, crush-resistant, shortenable, and extendable. The portion 112 is configured so that it does not cause significant discomfort even when it is pushed toward the nose 10 forcefully because it has some buffer effects from its spirally corrugated configuration. The mushroom-shaped or the dome-shaped base 110b will form a physical seal interface between the bottom surface of the nose 10 and the outer surface of the base 110b and prevent any further protrusion into the nostril 10b. The spirally corrugated configuration of the portion or tube 112 also creates a slight twisting force toward the nose 10 and helps form a physical seal between the top portion 114d of the first nasal insert 114 and the inner wall of the nostril 10b.

It should be appreciated that the portion or tube 112 of the first nasal insert 114 between the top portion 114d of the first nasal insert 114 and the base 110b can be a straight tube without any corrugations or a corrugated tube that is not spirally corrugated as long as it is flexible and crush-resistant and provides a good flexibility. The portion or tube 112 can be angled to align the first nasal insert 114 with the nasal air passageway in nose 10. However, the corrugated configuration is preferred, because it not only provides a good flexibility but also helps retain moisture and reduce upper airway dryness.

The tubular chamber 110, in at least one embodiment, is a hollow tube with or without a corrugated extendable configuration. The tubular chamber 110 is typically in fluid communication with the first nasal insert 114 through opening 112a and has a built-in gas supplying tubing or channel 116, a tube or portion 118, and an outlet 120 with a push-in connector. In at least one embodiment, the tubular chamber 110 is soft, flexible, crush-resistant, lightweight, transparent or semi-transparent. The tubular chamber 110, including the tube or portion 118, may be shaped in a way in which it fits the user's mustache area and/or the first nasal insert 114 can be inserted into either of nostrils 10a and 10b. It is placed beneath the user's nose 10 and above the user's the upper lip of the mouth 12. The tubular chamber 110 is built at a size that is large enough so that it can accommodate a part of the built-in tubing or channel 116 and allow to deliver gases during inhalation and discharge the exhaled gases during exhalation. The chamber 110 does not interfere with any manipulations in the mouth 12 such as endotracheal intubation in unconscious patients. The tubular chamber 110 does not cross the user's philtrum and will not obstruct the gas flow path of the other nostril 10a.

The portion or tube 118, which may be described as being part of the chamber 110, is located between the outlet 120 and the exit point 116e of the built-in tube 116, and may have a corrugated extendable configuration or a corrugated configuration. The portion or tube 118 preferably has an inner diameter of about 10 to 15 mm, which allows for gases being delivered or discharged. The portion or tube 118 may also be a straight tube without any corrugations, but a corrugated configuration is preferred. The corrugated configuration will help retain moisture and reduce upper airway dryness. The corrugated extendable configuration for tube 118 of the chamber 110 allows the tubular chamber 110 to be shortened when the patient is in a lateral position or extended for connecting to an anesthesia circuit or a CPAP valve when needed. When the tubular chamber 110 is extended (by extending the portion or tube 118), the volume of the tubular chamber 110 will be increased. The tubular chamber 110 can thus store more oxygen during exhalation. Alternatively, for the tubular chamber 110 without a corrugated extendable configuration, a flexible extendable tube adapter 122, shown in FIG. 1, can be attached to the outlet 120 of the tubular chamber 110. The outlet 120 of the tubular chamber 110 can be made in a way that it can accept both a push-in type tube adapter and a funnel type endotracheal tube adapter.

The flexible extendable tube adapter 122, in at least one embodiment, is a corrugated tube which has one connector on each end of its ends, i.e. a connector near end 120 and a connector near end 124 (FIG. 1). The connectors are compatible with the outlet 120 of the tubular chamber 110 and a standard anesthesia circuit at the end 124. The flexible extendable tube adapter 122 is typically soft, extendable, flexible, lightweight, and crush-resistant. It is used to connect the outlet 120 of the tubular chamber 110 to a CPAP valve or an anesthesia circuit. It can be shortened or extended when needed. When the adapter 122 is extended, its volume will be increased. The increased volume will store more oxygen during exhalation when high concentration of oxygen is needed.

The first open end 116a, shown in FIG. 2, of the built-in gas supplying tubing or channel 116 is located inside the base 110b of the first nasal insert 114 and the top portion of the tubular chamber 110. The base 110b, in at least one embodiment is in a mushroom shape or dome shape. In at least one embodiment, the base 110b is a hollow structure and also a part of the tubular chamber 110. Here for the description purpose, we call the base 110b a base but actually it also is a part of the tubular chamber 110. The outer diameter of the built-in gas supplying tubing or channel 116 preferably is equal to the opening 112a of the first nasal insert 114 or about half to two thirds of the opening 112a. The first open end 116a of the built-in tubing or channel 116 is close to the opening 112a but does not obstruct the opening 112a. It is constructed in a way that it has a very thin wall (may be about one third to half a millimeter or less), and a large internal diameter (may be up to about six to eight millimeters) which allows delivering high flow of gases and does not obstruct the gas flow path of the exhaled gases. The first open end 116a is beveled from its top side wall so that the delivered gases will be directed toward the opening 112a of the first nasal insert 114. The built-in tubing 116 is fixed to the inner wall of the base 110b and the top portion of the tubular chamber 110 via a few elastic bands or members 116b, 116c, and 116d, or molded to the inner wall of the base 110b and the tubular chamber 110. Alternatively, the built-in tubing or channel 116 can be curved inside the tubular chamber 110 and fixed or molded to the inner wall of the tubular chamber 110. The first open end 116a will be close to the second open end 112a of the first nasal insert 114 and the delivered gases will be directed toward the first nasal insert 114.

The second open end 116e of the built-in gas supplying tubing or channel 116 exits at the top side of the tubular chamber 110 near the base 110b and continues with the gas supplying tubing 104. The gas supplying tubing 104 is long enough and has a connecter that has a common configuration at its end so that the gas supplying tubing 104 can be connected to a gas supplying source.

The second nasal insert 106 includes a top portion 106d and a tube 106e. The tube 106e is a corrugated flexible and extendable tube and made from soft, non-irritating, inert materials, such as silicone or the like. Alternatively, the tube 106e can be a straight tube without any corrugations. The first open end 106a of the second nasal insert 106 has an inward rolled rim 106b with a few holes or slots 107 on it. These slots or holes 107 can prevent the mucosal tissue from being drawn onto the tip of the second nasal insert 106 at opening 106a and avoid the occlusion. The second nasal insert 106 has a much smaller diameter or width W2 than the first nasal insert 114's diameter or width W1. The top portion 106d preferably has an outer diameter W2 of about five to six millimeters and the tube 106e may have an outer diameter of about four to five millimeters. The width of the second nasal insert 106 does not obstruct the gas flow path of the nostril 10a and the second nasal insert 106 is dedicated for gas sampling. The tube 106e can be shortened, extended, or flexed in any part. Thus, the direction and the position of the second nasal insert 106 can be adjusted and hold for optimal gas sampling. The tube 106e and the top portion 106d are also soft and compliant and will not cause any discomfort when it is placed inside the nostril 10a. The second nasal insert 106 is attached to the tubular chamber 110 via an elastomeric band 110a and tube 108 or the like but the tube 106e of the second nasal insert 106 is not in fluid communication with the tubular chamber 110. I.e. 110a is not an opening and neither gas nor fluid flows from 110 through 110a into tube 108 or from tube 108 into chamber 110. The tube 108 may have an outer diameter of about six to eight millimeters (mm) and may be slightly larger than the tube 106e. The second open end 106c is connected to a tube 108 which is connected to the gas sampling tubing 102. The gas sampling tubing 102 is long enough and has a connector at one end that can be connect to the inlet of a gas analyzer The second nasal insert 106 of at least one embodiment of the present invention will allow more accurately monitoring the exhaled gases and avoid the common problems such as occlusion, improper position, and dislodgement.

A nasal plug, not shown, may have the same configuration as the first nasal insert 114 and the base 110b except that it does not have a gas flow path inside. It may have a mushroom-shaped top, similar to 114d, and a mushroom-shaped or a dome-shaped base, similar to 110b. It may have a portion 112 between the portion similar to top 114d and the portion similar to base 110b, and the portion similar to 112 may also be constructed in a spirally corrugated shape. Such a nasal plug, not shown, may be made from the inert, non-irritating, soft materials, such as silicone, or the like. It may be lightweight and resilient. The nasal plug, not shown, may be placed in the other nostril 10a when CPAP or positive pressure ventilation is needed. Before it is placed inside the other nostril 10a, the second nasal insert 106 is moved out of the nostril 10a. The nasal plug will form an airtight seal and prevent any air leak from the nostril 10a.

A detachable cap with a one-way valve can be attached to the outlet 120 of the tubular chamber 110 to prevent rebreathing and/or increase inhaled oxygen concentration. The detachable cap may be made from soft materials such as silicone or the like. There may be one connector on each end of the detachable cap. The connectors may be compatible with the outlet 120 of the tubular chamber 110. The one-way valve of the detachable cap, in at least one embodiment, only allows air to flow in one direction. By switching the direction of the detachable cap, the outlet 120 of the tubular chamber 110 can be completely blocked during exhalation or inhalation when high flow of oxygen is needed. When the outlet 120 is blocked during exhalation, the exhaled gases are not discharged via the tubular chamber 110 and there will be no rebreathing from the tubular chamber 110. When the outlet 120 is blocked during inhalation, exhaled gases are discharged via the outlet 120 during exhalation and there will be no air entry from the outlet 120 during inhalation.

For delivering low flow or high flow of oxygen, oxygen is delivered to the nasal airway via the first nasal insert 114 and the exhaled gases are discharged through the first nasal insert 114 and the other nostril 10a and sampled from the second nasal insert 106. To further save oxygen, the tube 118 of the tubular chamber 110 can be extended to increase the volume of the tubular chamber 110 and a detachable cap with a one-way valve can be applied to the outlet 120 of the tubular chamber 110 to avoid rebreathing. The tubular chamber 110 acts as an oxygen reservoir during exhalation. To further increase the oxygen reservoir volume, a flexible extendable tube adapter 122 can be attached to the outlet 120 of the tubular chamber 110. The delivered gases are directed to the nasal airway and there will be no gases leaking into the ambient air. For those patients who are not comfortable with the nasal insert 114 being placed inside the nostril 10b the top portion 114d of the first nasal insert 114 can be gently placed just outside of the nostril 10b. The top portion 114d of the first nasal insert 114 still can form a physical sealing interface around the opening of the nostril 10b when low flow or high flow of oxygen is delivered because of its unique configuration. After the patient is adequately sedated, the top portion 114d of the first nasal insert 114 can be placed inside the nostril 10b if needed.

For nasal insufflation, the gas supplying tubing 104 can be connected to one gas supplying source via a regular connector via end 104a or two gas supplying sources via a Y type connector. The outlet 120 of the tubular chamber 110 also can be connected to a gas supplying source. The total flow rate can reach up to fifty liters per minute (lpm), depending upon the gas supplying sources being used. Since there are no gases being wasted and all delivered gases are directed to the nasal airway via the first nasal insert 114, a much lower flow rate will be needed to achieve nasal insufflation. For a short period of time, humidification and heating are not necessary. For a prolonged period of time, a humidified gas can be delivered with the commercially readily available humidifiers. It will be very useful for preoxygenation during general anesthesia and emergency endotracheal intubation. It will increase the patient's comfort and decrease the incidents of hypoxemia. It also can be used as a rescue measure to decrease the chance for intubation or reintubation. The excessive gases escape from the other nostril 10a and the mouth 12, which decreases the anatomical dead spaces by flushing the nasal cavities, oropharynx, and oral cavity during the exhalation. It is less wasteful and significantly increases oxygen concentration during inhalation.

To attain CPAP, a CPAP valve is attached to the outlet 120 of the tubular chamber 110 via a flexible extendable tube adapter 122 and the gas supplying tubing 104 is connected to a gas supplying conduit of a CPAP machine while the other nostril 10*a* is blocked by a nasal plug. The supplying gases flow through the first nasal insert 114 and the exhaled gases are discharged via the nasal insert 114. The CPAP valve can be adjusted to achieve the desired level of CPAP. If used in a hospital setting, a CPAP machine may not be needed because a regular wall flow meter can deliver a gas flow up to thirty liters per minute (lpm) and attain a moderate CPAP level (eight to ten centimeters $H_2O$). Unlike other existing nasal interfaces (exit ports for exhalation near the nose), the exit port for exhalation can be placed far away from the patient's face and will significantly decrease the noises. The gases are delivered and discharged via the same nostril. This one-sided nasal CPAP configuration allows the patient to change his or her nostrils periodically. This will decrease the common side effects associated with the use of nasal CPAP such as dryness of nose and nasal congestion. The nasal breathing apparatus of one or more embodiments of the present invention is lightweight and does not need a support headgear or similar devices. It will be more comfortable for a patient to wear and will allow the patient to change head position freely. This will significantly increase patient comfort and compliance.

For nasal positive pressure ventilation, the outlet 120 of the tubular chamber 110 can be connected to an anesthesia circuit or a resuscitator bag via the flexible extendable tube adapter 122 with the gas supplying tubing 104 being blocked. There is no need, in at least one embodiment, for an additional face mask or nasal mask. To facilitate the nasal ventilation, the mouth 12 can be closed by a simple maneuver (chin left) and the airway can be opened by jaw thrust. The other nostril 10*a* can be blocked by a nasal plug or the pressure applied by a finger. It is easy to perform these maneuvers with the nasal breathing apparatus 100 of one or more embodiments of the present invention than with a face or nasal mask. For those patients with upper airway obstruction, a nasopharyngeal airway can be placed to relieve airway obstruction. The top portion 114*d* of the first nasal insert 114 can be inserted into the nasopharyngeal airway. Positive pressure ventilation can be achieved more easily and effectively.

For inhalational induction, an anesthesia circuit can be connected to the outlet 120 of the tubular chamber 110 or the gas supplying tubing 104 and the other nostril can be blocked with a nasal plug. The inhalational agents can be delivered into the patient's nasal airway via the first nasal insert 114. The patient can breathe through the nose 10 and the mouth 12. The patient can talk and communicate with the physicians during anesthesia induction. This will greatly decrease the patient's anxiety and enhance the comfort.

For delivering aerosol medications, the outlet 120 of the tubular chamber 110 or the gas supplying tubing 104 can be connected to a nebulizer. The exhale port of the nebulizer will be blocked and all aerosolized medication will be delivered into the nasal airway via the first nasal insert 114 during inhalation and exhalation. The patient can breathe through the other nostril 10*a*, the mouth 12 and/or the same nostril 10*b*. It will be more efficient to deliver aerosol medications with the apparatus 100 or 200 (to be described with reference to FIGS. 3 and 4) of embodiments of the present invention than with a face mask or a mouthpiece.

The nasal breathing apparatus 100 or 200 can be used for treating asthma and other conditions such as airway edema. Either of apparatus 100 or 200 can also be used for preparing airway for awake fiberoptic intubation. Either of apparatus 100 or 200 is particularly useful in those patients who are unable to cooperate or who are unable to breathe through the mouth. Either of apparatus 100 or 200 will increase patient comfort and compliance.

Figure 3:
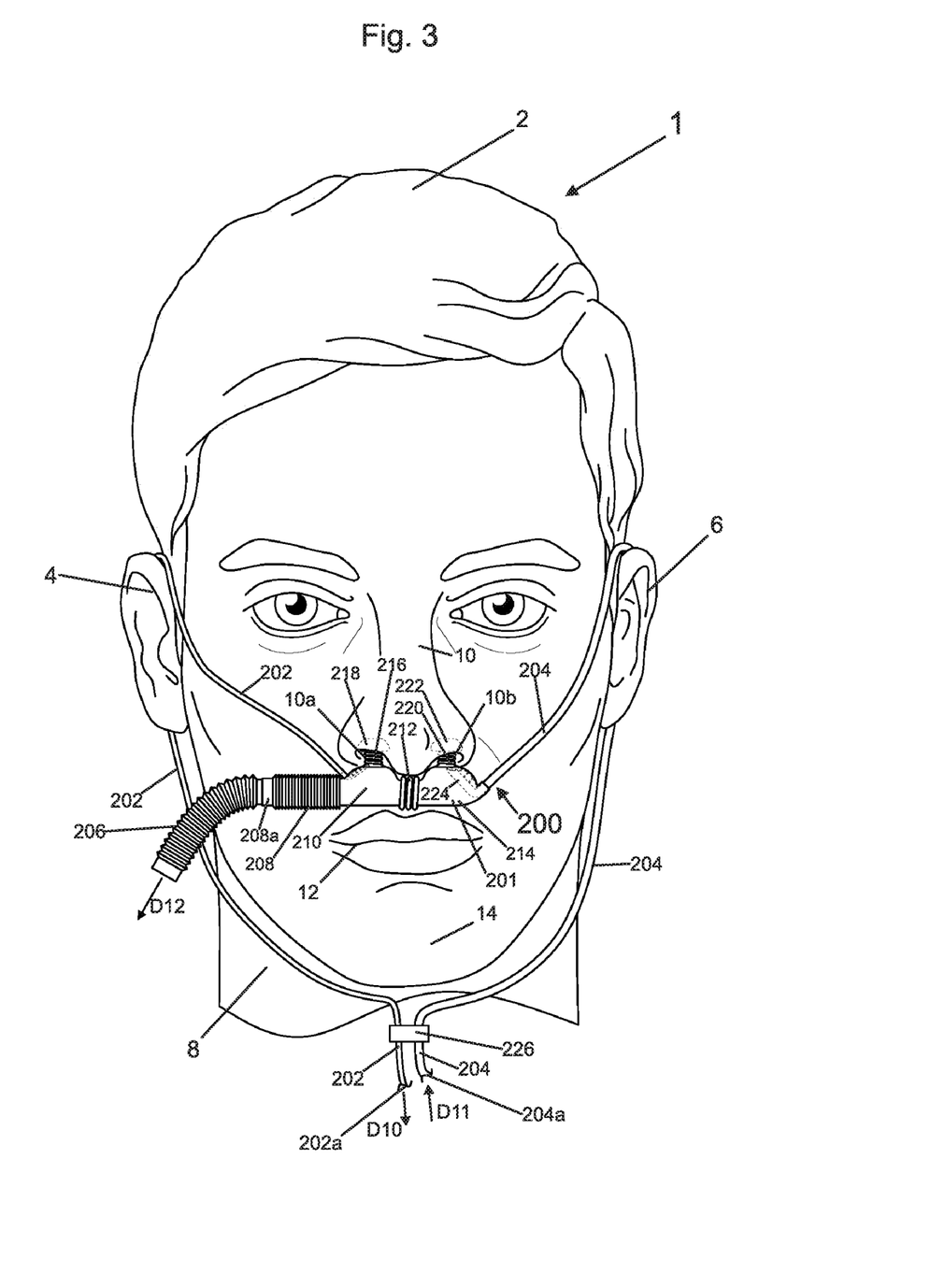
FIG. 3 shows a simplified diagram of a front view of a nasal breathing apparatus in accordance with another embodiment of the present invention being worn by a patient.

With reference to FIG. 3, the second preferred embodiment of the present invention is shown in which the person or patient 1 is wearing the apparatus 200 that is placed on the face beneath the nose 10 and above the upper lip of the mouth 12. The apparatus 200 has a main portion 201 which includes a first nasal insert 220 and a second nasal insert 216 and one tubular chamber 210. The main portion 201 is secured on the face with the loop formed by the gas supplying tubing 204 and the gas sampling tubing 202 hung on the back of the ears 6 and 4, respectively, as shown in FIG. 3. The loop is tightened to the patient's head by sliding a bolo type tie 226 or the like towards the patient's chin 14. The first nasal insert 220 is placed in the left nostril 10*b* (on the patient's left, on the right of FIG. 3) and the second nasal insert 216 in the right nostril 10*a* (on the patient's right, on the left of FIG. 3). Both nasal inserts form an airtight barrier in the corresponding nostrils. The gases are delivered to the nasal airway via the first nasal insert 220. The exhaled gases are discharged through both nasal inserts 220, 216 and sampled via the second nasal insert 216. The outlet 208*a* of the tubular chamber 210 is attached to a flexible extendable tube adapter 206 for discharging the exhaled gases or attaining CPAP/positive pressure ventilation.

Figure 4:
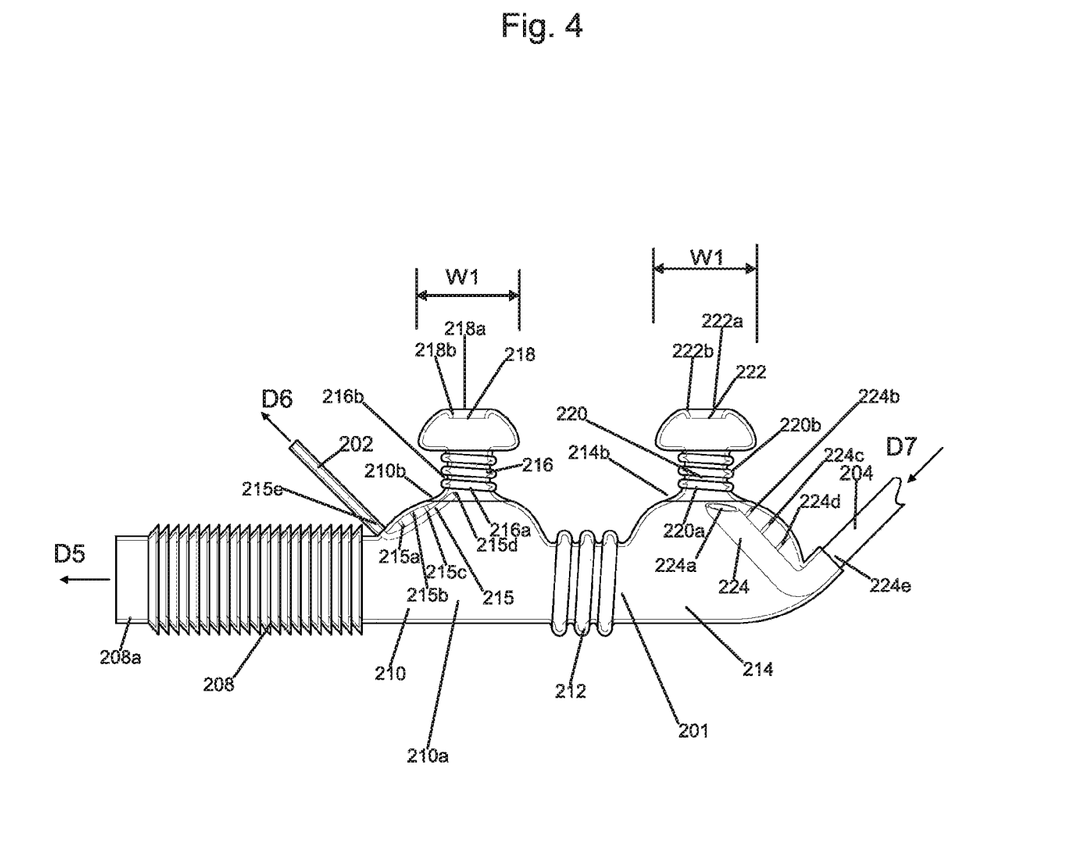
FIG. 4 shows a simplified diagram of a front view of part of the nasal breathing apparatus of FIG. 3.

FIG. 4 shows a simplified diagram of a front view of part of the nasal breathing apparatus 200 of FIG. 3. Both the first nasal insert 220 and the second nasal insert 116 include three parts or portions, i.e., a top portion (222, 218), a tube (220*b*, 216*b*), and a base (214*b*, 210*b*). They are manufactured integrally with the tubular chamber 210 (includes 208, 210*a*, 212, and 214) and in fluid flow communication with the tubular chamber 210 (includes 208, 210*a*, 212, and 214). Alternatively, they can be made separately and molded together. They should be soft, compliant, flexible, resilient, crush-resistant, lightweight and transparent or semi-transparent.

Both nasal inserts 220, 216 share the features and configurations of the first nasal insert 114 as described in the first embodiment of the present invention with reference to FIGS. 1 and 2. They have inward rolled rims 218*b* (for portion 218) and 222*b* (for portion 222), a mushroom-shaped top portion 222 for nasal insert 220 and top portion 218 for nasal insert 216, a mushroom-shaped or a dome-shaped base 210*b* for nasal insert 216 and mushroom-shaped or dome-shaped base 214*b* for nasal insert 220 and a spirally corrugated configuration 216*b* and 220*b* in the portion between the top portions 218 and 222 and the bases 210*b* and 214*b*. They are placed in each nostril and form an airtight seal within the corresponding nostrils. Their unique features and configurations permit them to have a very comfort fit and prevent the escape of gases from the nostrils.

It should be appreciated that the top portions 222 and 218 and the bases 214*b* and 210*b* of the first nasal insert 220 and the second nasal insert 216, respectively, can be formed in any other shape as long as they seal the nostrils and do not cause significant discomfort. Also the portion 216*b* or 220*b* between the top portion 218 or 222 and the base 210*b* or 214*b* of the nasal inserts can be a tube with or without a corrugated configuration. However, a corrugated configuration is preferred because it not only provides a good flexibility but also helps retain moisture and reduce upper airway dryness. They can be angled in a way that they align the nasal inserts with the nasal air passageways.

The tubular chamber 210 (includes 208, 210a, 212, and 214) is a corrugated hollow tube or a hollow tube with a few corrugations in portion 212 between the nasal insert 216 and the nasal insert 220. The tubular chamber 210 (includes 208, 210a, 212, and 214) is soft, flexible, crush-resistant, lightweight and transparent or semi-transparent. The corrugations in portion 212 make the tubular chamber 210 (includes 208, 210a, 212, and 214) more flexible and allow the optimal positioning of the nasal inserts 220 and 216.

The top side of the tubular chamber 210 continues with the bases 210b, 214b of the nasal inserts 216, and 220 and is in fluid communication with both nasal inserts 220, 216. The portion 208 between the outlet 208a of the tubular chamber 210 and the second nasal insert 216 can have a corrugated extendable configuration or a corrugated configuration. It also can be a straight tube without any corrugations. However, a corrugated configuration is preferred, because it will help retain moisture and reduce upper airway dryness. The corrugated extendable configuration of portion 208 allows the tubular chamber 210 to be shortened when the patient is in a lateral position or extended for connecting to an anesthesia circuit or a CPAP valve when needed. When the tubular chamber 210 is extended, the volume of the tubular chamber 210 will be increased. The tubular chamber 210 can store more oxygen during exhalation. Alternatively, for the tubular chamber 210 without a corrugated extendable configuration, a flexible extendable tube adapter 206 can be attached to the tubular chamber 210 as shown in FIG. 3.

The tubular chamber 210 has two built-in tubings or channels 224, and 215 and one outlet 208a. The outlet 208a shown in FIG. 4 has a connector which is compatible with an anesthesia circuit, the flexible extendable tube adapter 206 in FIG. 3 and an endotracheal tube adapter. The outlet 208a is the common pathway for the gases entering into the nasal inserts during inhalation and for discharging the exhaled gases from the nasal inserts during exhalation. It can be connected to a CPAP valve or anesthesia circuit when CPAP or nasal positive pressure ventilation needed.

The built-in tubing or channel 224 has a very thin wall (may be about one third to half of a millimeter (mm) or less) and its outer diameter is equal to the inner diameter of the tube 220b or about half to two thirds of the inner diameter of the tube 220b. The built-in tubing 224 is fixed to the inner wall of the base 214b and the tubular chamber 214 via elastic bands 224b, 224c, and 224d, or members or molded to the inner wall of the base 214b. The first open end 224a of the built-in tubing or channel 224 is located in the base 214b of the first nasal insert 220 and beveled from its top side wall. The beveled open end 224a will direct the gases flow toward the nasal insert 220 and not to the outlet 208a of the tubular chamber 210. It allows delivering high flow of gases and discharging the exhaled gases via the nasal insert 220. Alternatively, the first open end 224a of the built-in tubing or channel 224 can be located at any position within the nasal insert 220 or the portion 214 as long as it allows delivering high flow of gases and discharging the exhaled gases via the nasal insert 220.

The built-in tubing or channel 215 within the nasal insert 216 may have a relatively rigid wall to avoid collapse caused by the suction force during the gases sampling. The first open end 215d can be located inside the portion between the bottom of the top portion 218 and the base 210b. The built-in tubing 215 may be attached to the inner wall of the base 210b via a few elastic bands 215a, 215b, and 215c, or molded to the inner wall of the second nasal insert 216. The outer diameter of the built-in tubing or channel 215 within the second nasal insert 216 is much smaller and may be less than one fifth to one third of the inner diameter of the tube 216b of the second nasal insert 216 to facilitate the discharge of the exhaled gases.

Alternatively, both the built-in gas supplying tubing or channel 224 and the built-in gas sampling tubing or channel 215 may have the same outer diameter or different diameters. However, they should not exceed more than 50% the inner diameter of the tubes 216b and 220b in order to facilitate discharging the exhaled gases. The device also can be constructed in a way in which the built-in tubing or channel 224 within the first nasal insert 220 or portion 214 is dedicated for sampling and discharging the exhaled gases while the built-in tubing or channel 215 within the second nasal insert 216 or portion 210a is mainly used for delivering gases. Both the built-in tubings or channels 224 and 215 within the nasal inserts or portions of the tubular chamber 210 can be the same size and used for delivery of gases.

The second open ends 224e and 215e of the built-in tubing or channels 224 and 215 exit on the top side of the tubular chamber 210 and is continued with a gas supplying tubing 204 or a gas sampling tubing 202. The gas supplying tubing 204 and the gas sampling tubing 202 form a loop which can be hung around the back of the ears 6,4 or the head 2 of a person 1, to secure the apparatus 200. Alternatively, the apparatus 200 can be secured on the face by a head strap system or other means such as adhesive cushion. The gas supplying tubing 204 and the gas sampling tubing 202 are long enough and have the connector at their other ends that can be connected to a gas supplying source or an inlet of a gas analyzer.

When low flow or high flow of oxygen is delivered, oxygen is delivered to the nasal airway via the first nasal insert 220 from the gas supplying tubing 204 and the exhaled gases are sampled from the second nasal insert 216. It conserves oxygen because oxygen is directed toward the nasal airway and there is no air leak from the nostrils. It also allows more accurately monitoring $ETCO_2$ because the exhaled gases are sampled from the second nasal insert 216 and there is no dilution from the delivered oxygen and the ambient air. Although both nostrils are sealed with the nasal inserts 220, 216, the nostrils are open to ambient through the outlet 208a of the tubular chamber 210. The patient can comfortably breathe through the nose without being impeded by the device.

When high concentration of oxygen is needed, the outlet 208a of the tubular chamber 210 can be attached to a detachable cap with one-way valve. It will avoid air dilution from air entry during inhalation. Alternatively, the outlet 208a shown in FIG. 4, can be attached to a flexible extendable tube adapter 206 shown in FIG. 3, to increase the reservoir volume. In at least one embodiment, both the gas supplying tubing 204 and the gas sampling tubing 202 can be connected to oxygen sources. The total gas flow rate can reach more than fifty lpm.

To attain a CPAP, the gas supplying tubing 204 or both the gas supplying tubing 204 and the gas sampling tubing 202 can be connected to a gas supplying conduit from a CPAP machine or a gas supplying source and the outlet 208a can be connected to a CPAP valve. The gases flow into the first nasal insert 220 or both nasal inserts 220, 216 and are discharged via the second nasal insert 216 and the first nasal insert 220. To achieve positive pressure ventilation, an anesthesia circuit or a resuscitator bag can be connected to the outlet 208a directly or via a flexible extendable tube adapter 206 with the gas supplying tubing 204 and the gas sampling tubing 202 being blocked.

To deliver aerosol medications, a nebulizer can be attached to the gas supplying tubing 204 or the outlet 208*a* of the tubular chamber 210. The patient can breathe through the nose and the mouth. To perform inhalational induction, an anesthesia circuit can be connected to the outlet 208*a* of the tubular chamber 210 or the gas supplying tubing 204. The second embodiment of the present invention has all functions as the first embodiment.

Generally speaking, referring to FIG. 3, gases flow in the direction D11 into end 204*a* of tubing 204, through tubing 204, into chamber 214, and out component 222, into the nasal airway. In addition, gas flows from the components 220 and 216 into the chamber 210, then into components 208 and 206 and out in the direction D12. Gas also flows from the nose 10 into the component 218, then into tubing 202, and then out end 202*a* in the direction D10.

Generally speaking, as shown in FIG. 4, gasses flow in tubing 204 in the direction D7, flow out of the tubing 202 in the direction D6, and flow out of component 208*a* in the direction D5.

Although the invention has been described by reference to particular illustrative embodiments thereof, many changes and modifications of the invention may become apparent to those skilled in the art without departing from the spirit and scope of the invention. It is therefore intended to include within this patent all such changes and modifications as may reasonably and properly be included within the scope of the present invention's contribution to the art.

I claim:

1. A nasal breathing apparatus comprising
a first nasal insert that is configured to be at least partially placed inside a first nostril of a nose of a human being and thereby adapted to form an airtight barrier with an inner wall of the first nostril of the nose for delivering gases to a nasal airway inside of the nose and discharging the exhaled gases from the first nostril;
a second nasal insert that is configured to be placed at least partially inside a second nostril of the nose of the human being and thereby adapted to form an airtight barrier with an inner wall of the second nostril of the nose for delivering gases to a nasal airway inside of the nose and discharging the exhaled gases from the second nostril; and
a tubular chamber which is in fluid communication with the first nasal insert and the second nasal insert;
wherein the tubular chamber includes a first portion that is connected to the first nasal insert, a second portion that is connected to the second nasal insert, and a third portion which connects the first portion to the second portion;
wherein a top base of the first portion of the tubular chamber also forms a bottom base of the first nasal insert and is adapted to seal an opening of the first nostril;
wherein a top base of the second portion of the tubular chamber also forms a bottom base of the second nasal insert and is adapted to seal an opening of the second nostril;
wherein the tubular chamber includes a first built-in tubing that has a first open end in the first nasal insert and which is fixed at a location spaced apart from the first open end of the first built-in tubing to the top base of the first portion of the tubular chamber for delivering gases to the first nasal insert;
wherein the tubular chamber includes a second built-in tubing that has a first open end in the second nasal insert and which is fixed at a location spaced apart from the first open end of the second built-in tubing to the top base of the second portion of the tubular chamber for sampling gases;
wherein the tubular chamber includes a first outlet for discharging and delivering gases and for providing continuous positive airway pressure and positive pressure ventilation;
wherein the tubular chamber includes a first hollow tube which is located between a second end of the second built-in tubing, opposite the first end of the second built-in tubing and the outlet of the tubular chamber;
wherein the first end of the first built-in tubing is located inside the top base of the first portion of the tubular chamber and beveled from a top side wall of the first built-in tubing which directs delivered gases toward the first nasal insert through the first end of the first built-in tubing and a second end of the first built-in tubing, opposite the first end of the first built-in tubing, is configured to be connected to a gas supplying tubing for attaching to a gas supplying source; and
wherein the first end of the second built-in tubing is located inside the top base of the second portion of the tubular chamber and configured to sample gases from the second nasal insert and the second end of the second built-in tubing is configured to be connected to a gas sampling tubing for attaching to a gas analyzer.

2. The nasal breathing apparatus of claim 1, wherein
the first nasal insert includes a mushroom-shaped top portion, the bottom base which is mushroom-shaped, and a spirally corrugated tube which connects the mushroom-shaped top portion of the first nasal insert to the mushroom-shaped bottom base of the first nasal insert; and
wherein the second nasal insert includes a mushroom-shaped top portion, the bottom base which is mushroom-shaped, and a spirally corrugated tube which connects the mushroom-shaped top portion of the second nasal insert to the mushroom-shaped bottom base of the second nasal insert.

3. The nasal breathing apparatus of claim 2, wherein
the mushroom-shaped top portion of the first nasal insert is configured to be placed inside the first nostril and adapted to create a sealing interface between an outer surface of the mushroom-shaped top portion of the first nasal insert and the inner wall of the first nostril for delivering gases and discharging exhaled gases; and
the mushroom-shaped top portion of the second nasal insert is configured to be placed inside the second nostril and adapted to create a sealing interface between an outer surface of the mushroom-shaped top portion of the second nasal insert and the inner wall of the second nostril for delivering gases and discharging exhaled gases.

4. The nasal breathing apparatus of claim 2, wherein
the first nasal insert includes a first open end having an inward rolled rim which is resilient and which is adapted to form an airtight sealing interface between the inward rolled rim and the inner wall of the first nostril which prevents the leakage of gases;
the second nasal insert includes a first open end having an inward rolled rim which is resilient and which is adapted to form an airtight sealing interface between the inward rolled rim and the inner wall of the second nostril which prevents the leakage of gases;

wherein the spirally corrugated tube of the first nasal insert is a flexible and crush-resistant, shortenable, and extendable tube which allows adjusting the direction and position of the first nasal insert; and wherein the spirally corrugated tube of the second nasal insert is a flexible and crush-resistant, shortenable, and extendable tube which allows adjusting the direction and position of the second nasal insert.

5. The nasal breathing apparatus of claim 2, wherein the mushroom-shaped bottom base of the first nasal insert is configured to be placed against the opening of the first nostril and thereby is adapted to form a physical sealing interface between a bottom surface of the nose and an outer surface of the mushroom-shaped bottom base of the first nasal insert to seal the opening of the first nostril and to prevent the leakage of gases from the first nostril and further protrusion of the first nasal insert into the first nostril; and the mushroom-shaped bottom base of the second nasal insert is configured to be placed against the opening of the second nostril and thereby is adapted to form a physical sealing interface between a bottom surface of the nose and an outer surface of the mushroom-shaped bottom base of the second nasal insert to seal the opening of the second nostril and to prevent the leakage of gases from the second nostril and further protrusion of the second nasal inserts into the second nostril.

6. The nasal breathing apparatus of claim 1, wherein the tubular chamber is a corrugated hollow tube which is formed integrally with the first and the second nasal inserts; and wherein the tubular chamber is in fluid communication with the first and the second nasal inserts; and wherein the tubular chamber has an outlet that has a connecter which is compatible with an anesthesia circuit for continuous positive airway pressure and positive pressure ventilation.

7. The nasal breathing apparatus of claim 6, wherein the tubular chamber is configured so that the first portion, the second portion, and the third portion of the tubular chamber fit in a space between the nose and an upper lip of a mouth of the human being when the first nasal insert and the second nasal insert are placed inside the corresponding nostrils.

8. The nasal breathing apparatus of claim 1, wherein the first portion of the tubular chamber is configured so that it accommodates the first built-in tubing and allows the delivery of gases to and from the first nasal insert and the third portion of the tubular chamber;

wherein the second portion of the tubular chamber is configured so that it accommodates the second built-in tubing and allows the delivery of gases to and from the second nasal insert and the third portion of the tubular chamber; and wherein the third portion of the tubular chamber is configured to be smaller in diameter than the first portion and the second portion of the tubular chamber so that the third portion of the tubular chamber allows delivering gases to and from the first portion and the second portion of the tubular chamber.

9. The nasal breathing apparatus of claim 1, wherein the first portion of the tubular chamber has a first side and a second side which is opposite to the first side of the first portion of the tubular chamber;

wherein the first side of the first portion of the tubular chamber is connected to the third portion of the tubular chamber;

wherein the second end of the first built-in tubing is connected to the first portion of the tubular chamber on the second side of the first portion of the tubular chamber;

wherein the second portion of the tubular chamber has a first side and a second side which is opposite to the first side of the second portion of the tubular chamber;

wherein the first side of the second portion of the tubular chamber is connected to the third portion of the tubular chamber; and wherein the first hollow tube is connected to the second portion of the tubular chamber on the second side of the second portion of the tubular chamber.

10. The nasal breathing apparatus of claim 1, wherein a part of the first hollow tube is a flexible and extendable corrugated tube that is retractable and extendable; and wherein the first hollow tube is configured to allow delivering gas to and from the first portion, the second portion, and the third portion of the tubular chamber.

11. The nasal breathing apparatus of claim 1, wherein the first built-in tubing is fixed to the top base of the first portion of the tubular chamber by at least one member;

wherein the at least one member has a first end that is fixed to the first built-in tubing and a second end that is fixed to the top base of the first portion of the tubular chamber;

wherein the second built-in tubing is fixed to the top base of the second portion by at least one member; and wherein the at least one member has a first end that is fixed to the second built-in tubing and a second end that is fixed to the top base of the second portion of the tubular chamber.

12. The nasal breathing apparatus of claim 1 further comprising:

the gas supplying tubing; and the gas sampling tubing; wherein the first built-in tubing and the gas supplying tubing are configured to allow the delivery of high flow of gases to the first nasal insert; and wherein the second built-in tubing and the gas sampling tubing are configured to be smaller than the first built-in tubing so that it does not obstruct the flow path inside the second nasal insert and the second portion of the tubular chamber and allows sampling exhaled gases from the second nasal insert.

13. The nasal breathing apparatus of claim 1, further comprising the gas supplying tubing;

and the gas sampling tubing; and wherein the gas supplying tubing and the gas sampling tubing are configured to be hung on the back of the ears for securing the nasal breathing apparatus to a face of the human being.

14. The nasal breathing apparatus of claim 1, wherein the first portion of the tubular chamber has a width;

wherein the second portion of the tubular chamber has a width;

wherein the third portion of the tubular chamber has a width;

wherein the width of the third portion of the tubular chamber is smaller than that of the first portion and the second portion of the tubular chamber;

wherein the first hollow tube has an outer diameter parallel to the width of the second portion of the tubular chamber; and wherein the width of the second portion of the tubular chamber is greater than the outer diameter of the first hollow tube.

15. A nasal breathing apparatus comprising a first nasal insert that is configured to be at least partially placed inside a first nostril of a nose of a human being and thereby adapted to form an airtight barrier with an inner wall of the first nostril of the nose for delivering gases to a nasal airway inside of the nose and discharging the exhaled gases from the first nostril;

a second nasal insert that is configured to be placed at least partially inside a second nostril of the nose of the human being and thereby adapted to form an airtight barrier with an inner wall of the second nostril of the nose for delivering gases to a nasal airway inside of the nose and discharging the exhaled gases from the second nostril; and a tubular chamber which is in fluid communication with the first nasal insert and the second nasal insert;

wherein the tubular chamber includes a first portion that is connected to the first nasal insert, a second portion that is connected to the second nasal insert, and a third portion which connects the first portion to the second portion;

wherein a top base of the first portion of the tubular chamber also forms a bottom base of the first nasal insert and is adapted to seal an opening of the first nostril;

wherein a top base of the second portion of the tubular chamber also forms a bottom base of the second nasal insert and is adapted to seal an opening of the second nostril;

wherein the tubular chamber includes a first built-in tubing that has a first open end in the first nasal insert and which is fixed at a location spaced apart from the first open end of the first built-in tubing to the top base of the first portion of the tubular chamber for sampling gases from the first nasal insert;

wherein the tubular chamber includes a second built-in tubing that has a first open end in the second nasal insert and which is fixed at a location spaced apart from the first open end of the second built-in tubing to the top base of the second portion of the tubular chamber for delivering gases to the second nasal insert;

wherein the first built-in tubing is fixed to the top base of the first portion of the tubular chamber by at least one member;

wherein the at least one member has a first end that is fixed to the first built-in tubing and a second end that is fixed to the top base of the first portion of the tubular chamber;

wherein the second built-in tubing is fixed to the top base of the second portion by at least one member;

wherein the at least one member has a first end that is fixed to the second built-in tubing and a second end that is fixed to the top base of the second portion of the tubular chamber;

wherein the tubular chamber includes a first outlet for discharging and delivering gases and for providing continuous positive airway pressure and positive pressure ventilation; and wherein the tubular chamber includes a first hollow tube which is located between a second end of the second built-in tubing, opposite the first end of the second built-in tubing, and the outlet of the tubular chamber.

16. The nasal breathing apparatus of claim 15, wherein the first built-in tubing and the second built-in tubing are configured in a way so that they do not obstruct the air flow paths in the first nasal insert and the second nasal insert and allow delivering gases to and discharging gases from the first nasal insert and the second nasal insert;

wherein the first built-in tubing is configured to be smaller than the second built-in tubing and used for sampling gases from the first nasal insert; and wherein the second built-in tubing is configured to allow the delivery of high flow of gases to the second nasal insert.

* * * * *